United States Patent [19]

Smith et al.

[11] Patent Number: 5,254,109
[45] Date of Patent: Oct. 19, 1993

[54] SEPARATELY PACKAGED APPLICATOR PADS FOR TOPICAL DELIVERY OF INCOMPATABLE DRUGS

[75] Inventors: James A. Smith, Chatham, Mass.; Betty J. Murphy, Upper Montclair, N.J.

[73] Assignee: Creative Products Resource Associates, Ltd., North Caldwell, N.J.

[21] Appl. No.: 986,598

[22] Filed: Dec. 7, 1992

[51] Int. Cl.[5] .................................... A61M 35/00
[52] U.S. Cl. ................................ 604/289; 604/290; 604/304; 128/743; 602/57; 401/132; 514/859
[58] Field of Search ............... 128/743; 15/104.93; 602/57; 604/289, 290, 309, 310, 19, 304; 206/223, 441, 568, 570; 424/78.07; 514/164, 85.9; 401/132

[56] References Cited

U.S. PATENT DOCUMENTS

| | | |
|---|---|---|
| 1,637,153 | 7/1927 | Lawton . |
| 2,102,858 | 12/1937 | Schlumbohm . |
| 2,621,784 | 12/1952 | Van Boytham . |
| 2,760,630 | 8/1956 | Lakso . |
| 2,932,841 | 4/1960 | Graves . |
| 2,933,431 | 4/1960 | Sperouleas . |
| 2,999,265 | 9/1961 | Duane et al. . |
| 3,053,385 | 9/1962 | Spees . |
| 3,082,468 | 3/1963 | Wattles . |
| 3,196,478 | 7/1965 | Baymiller et al. . |
| 3,224,640 | 12/1965 | Schneider et al. . |
| 3,240,326 | 3/1966 | Miller . |
| 3,280,420 | 10/1966 | Wanzanberg . |
| 3,323,640 | 6/1967 | Kugler . |
| 3,369,267 | 2/1968 | Friedland et al. . |
| 3,403,776 | 10/1968 | Denny . |
| 3,485,349 | 12/1969 | Chaney, Jr. . |
| 3,527,400 | 9/1970 | Shepherd et al. . |
| 3,561,456 | 2/1971 | Stuart, Jr. . |
| 3,608,566 | 9/1971 | Storandt . |
| 3,608,708 | 9/1971 | Storandt . |
| 3,613,879 | 10/1971 | Kemble . |
| 3,616,898 | 11/1971 | Massle . |
| 3,635,567 | 1/1972 | Richardson, Jr. . |
| 3,647,305 | 3/1972 | Baker et al. . |
| 3,826,259 | 7/1974 | Bailey . |
| 3,889,804 | 6/1975 | Ravich .................. 401/132 |
| 3,903,345 | 9/1975 | Baker et al. . |
| 3,921,802 | 11/1975 | Thompson . |
| 3,981,304 | 9/1976 | Szpur . |
| 3,986,640 | 10/1976 | Redmond . |
| 4,140,409 | 2/1979 | DeVries . |
| 4,265,234 | 5/1981 | Schaar . |
| 4,281,640 | 8/1981 | Spiegelberg ............ 602/57 |
| 4,332,319 | 6/1982 | Hurwood . |
| 4,355,028 | 10/1982 | Kligman ................ 514/164 |
| 4,372,098 | 2/1983 | Mason . |
| 4,427,111 | 1/1984 | Laipply . |
| 4,427,115 | 1/1984 | Laipply . |
| 4,430,013 | 2/1984 | Kaufman . |

(List continued on next page.)

FOREIGN PATENT DOCUMENTS 613023 1/1961 Canada .
3105247 8/1982 Fed. Rep. of Germany .

OTHER PUBLICATIONS

J. F. Hanlon, "Coatings and Laminations," in *Handbook of Package Engineering* (2d ed.), pp. 4-1 to 4-20 (1984).
Mason-Keller Corporation Information Release entitled "M-K Applicator Package" (Apr. 24, 1978).

*Primary Examiner*—Randall L. Green
*Assistant Examiner*—Paul Prebilic
*Attorney, Agent, or Firm*—Merchant, Gould, Smith, Edell, Welter & Schmidt

[57] ABSTRACT

The present invention provides a method for applying a plurality, preferably two, dermatological agents to the skin from a single dispensing and applicator system comprising a plurality of compartmentalized applicator pads which may be exposed and sequentially applied to the afflicted skin area.

35 Claims, 4 Drawing Sheets

U.S. PATENT DOCUMENTS

| | | | |
|---|---|---|---|
| 4,497,794 | 2/1985 | Klein et al. . | |
| 4,511,533 | 4/1985 | Guadagno et al. . | |
| 4,559,157 | 12/1985 | Smith et al. . | |
| 4,570,820 | 2/1986 | Murphy . | |
| 4,648,506 | 3/1987 | Campbell . | |
| 4,690,821 | 9/1987 | Smith . | |
| 4,692,329 | 9/1987 | Klein et al. . | |
| 4,696,393 | 9/1987 | Laipply . | |
| 4,751,934 | 6/1988 | Moir et al. | 401/132 |
| 4,762,124 | 8/1988 | Kerch et al. . | |
| 4,796,751 | 1/1989 | Madkour | 206/205 |
| 4,806,572 | 2/1989 | Kellet . | |
| 4,812,067 | 3/1989 | Brown et al. . | |
| 4,896,768 | 1/1990 | Anderson . | |
| 4,901,851 | 2/1990 | Gerry . | |
| 4,915,102 | 4/1990 | Kwiatek et al. | 602/57 |
| 4,915,228 | 4/1990 | Johns | 602/57 |
| 5,145,675 | 9/1992 | Won | 424/78.02 |

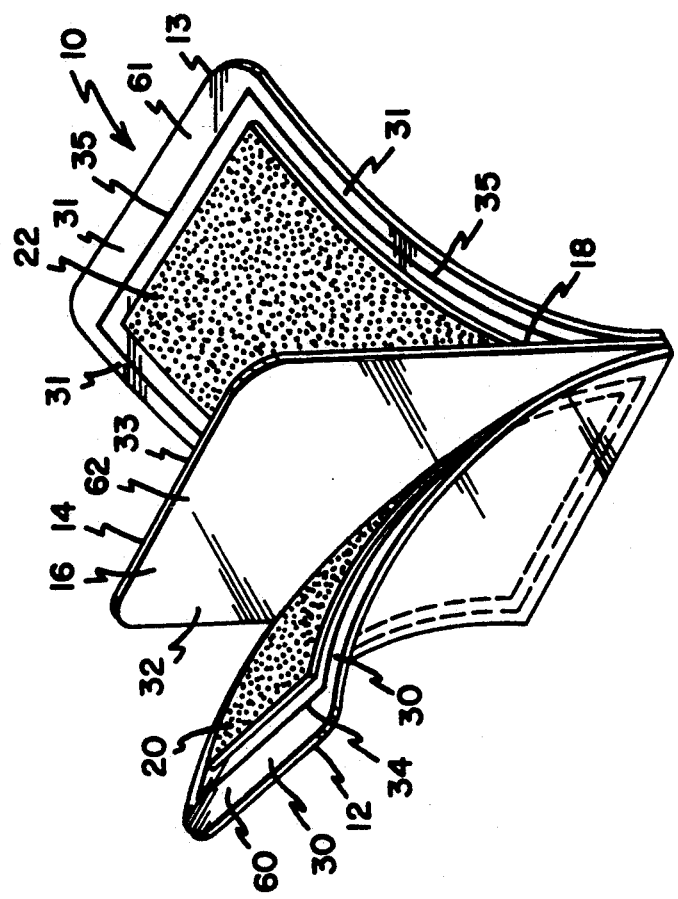
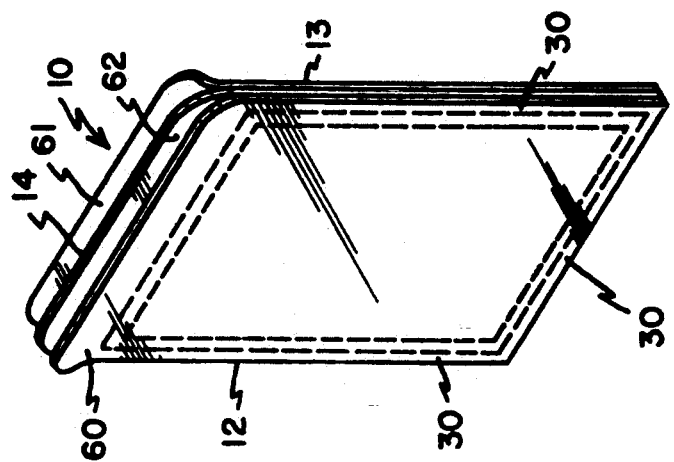

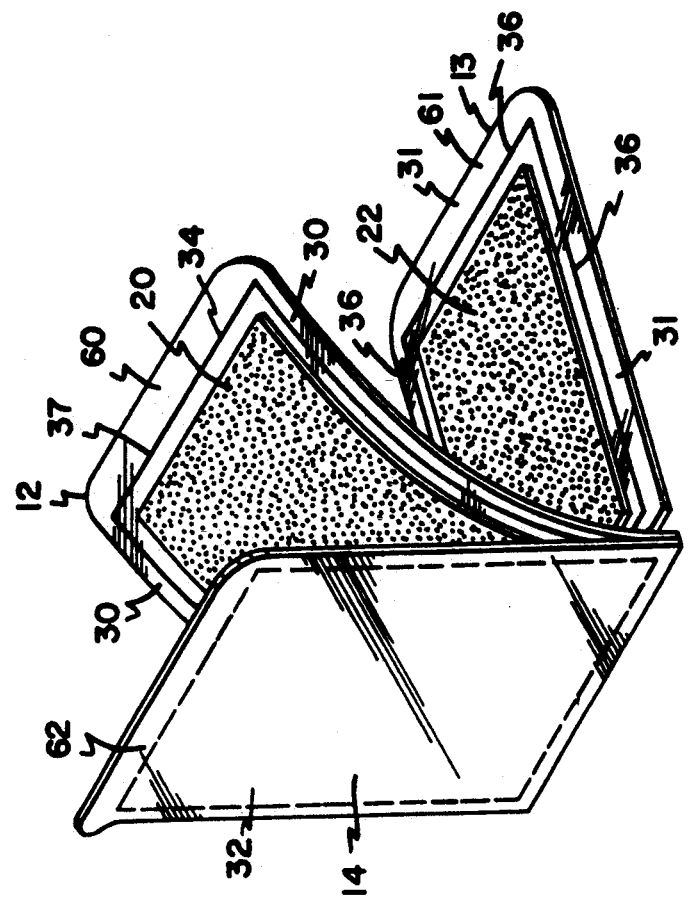
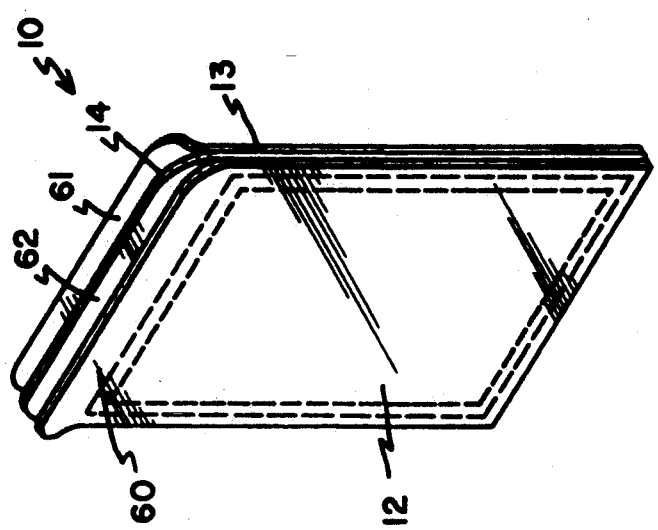

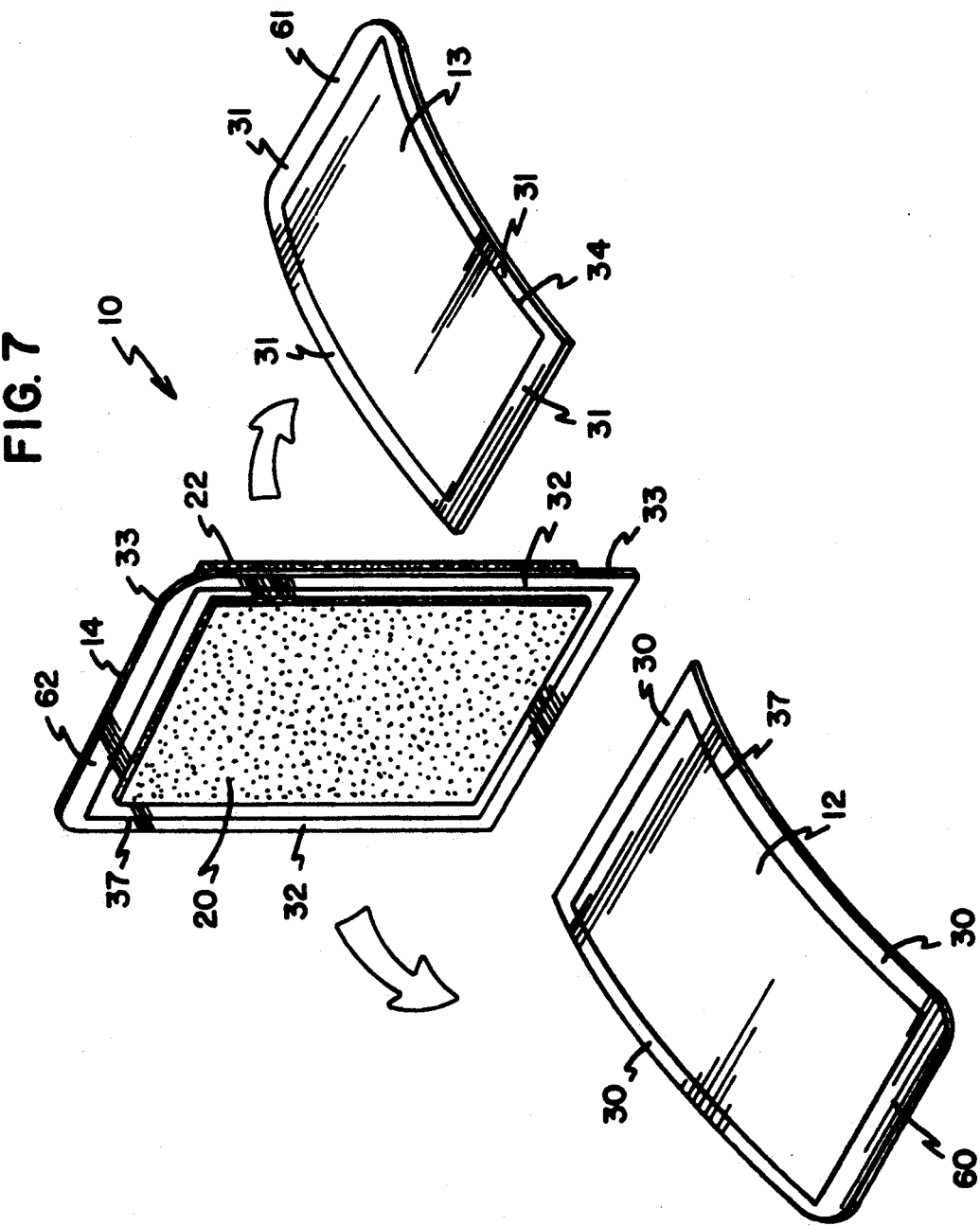

SEPARATELY PACKAGED APPLICATOR PADS FOR TOPICAL DELIVERY OF INCOMPATABLE DRUGS

FIELD OF THE INVENTION

The invention is directed to a method for containing protecting, dispensing and applying substances such as solid and flowing substances, and more particularly, to a method for dispensing and applying two or more dermatological agents either simultaneously or sequentially.

BACKGROUND OF THE INVENTION

A wide variety of packages are used to contain and protect a substance until it is desired to release and dispense the substance from the package. Several methods exist for dispensing and applying various solid substances or articles, such as powders, pills, granules and other shaped substances. Said methods may also be used to dispense and apply various flowable substances such as gels, solutions, dispersions, and other dimensionally unstable substances. In some cases, it may be desirable to include structure as part of the package which assists in dispersing or applying the contents. Oftentimes, the package includes an applicator for directed application of the contents, as they are dispensed from the package.

Several factors are taken into consideration in providing a method for dispensing a flowable or solid substance. One concern is the performance characteristics of the dispensing package. For example, the ease with which the package can be opened and its contents expelled can be important. The ability of the package to store and contain a substance prior to its application is another factor. When an applicator such as an absorbent pad or sheet is included as part of the package, secure attachment of the applicator to the packaging can be important so that the applicator does not become disengaged during use.

Various packages have been developed to contain and dispense solutions, dispersions or gels of various active ingredients. One such dispenser is an envelope-like package that defines an internal reservoir for containing a fluid. For example, U.S. Pat. No. 4,427,115 to Laipply, discloses a packaging device for applying various fluids to the skin. The device is made of a flexible sheet of fluid impermeable material that is folded in half and sealed around the edges in a temporary seal. The two halves of the sheet are pulled apart to break the seal and form a flat surface covered with the fluid. An absorbent pad may be adhered inside the chamber to aid in the retention and delivery of the fluid.

Other packaging systems provide for a cup-like reservoir with a foil or paper covering that is torn off to expose the fluid or other material contained within the chamber. For example, Canadian Patent No. 613,023 to Wilson et al. discloses a creamer-type dispenser with a wide-mouthed cup and a covering sheet sealed over the mouth of the cup. The covering sheet has a tab adhesively sealed over a flat extension of the rim of the cup. The package is opened by pulling the tab of the covering sheet upward off the rim extension and inward toward the cup. U.S. Pat. No. 3,860,348 to Doyle et al. discloses a cup with a foil covering over the mouth and a liquid-impregnated sponge attached to the inside of the cup. When the covering is peeled off the rim of the cup, the sponge projects outward through the opening.

U.S. Pat. No. 4,372,098, to Mason discloses an applicator package with a pair of side panels, one of which has a recessed portion for receiving an absorbent pad which is secured to the side panel within the central recessed portion. The applicator means sealed within the package by sealing the edged portion of the side panel in surrounding relation to the applicator means thereby enclosing and hermetically sealing the applicator means within the side panels. One of the edged portions of the side panels is then secured to enable the side panels to be gripped at that area and separated from each other so as to expose the applicator means.

Packages have also been developed to expel the contents of an inner chamber through a fracture or score line in one surface of the package. The ends of the package are forced together to expand and rupture the score line. For example, U.S. Pat. No. 3,968,630 to Redmond discloses a dispensing package having a single reservoir with a pattern of perforations cut partially through the surface on one side of the package that is covered with a foil sealant.

U.S. Pat. No. 4,796,751 to Madkour discloses a portable eyeglass cleaning kit which comprises a generally flat flexible container having two separate compartments which are separably operable to make separably available the lens cleaning medium and the lens wiping medium. The cleaning and wiping media absorbent material such as woven or unwoven fabric or tough liquid absorbent paper. The cleaning and wiping media are not affixed to the container and are separably removable from the compartments of the container. The container is made of a moisture and gas impervious sheet material such as metal foil, treated paper or plastic film. the container is operable by tearing along a scored line or by separation of the sealed edges.

A further consideration in designing a useful dispensing system is the ability to deliver more than one substance from a unitary system. Also desirable is a packaging system that is useful to simultaneously combine and dispense a plurality of substances, each requiring separate storage until being combined, due to their physical or chemical incompatibility.

To accomplish this, several applicator systems with a prescored fracture line in one surface of a package provide for reservoirs in discrete portions of a single package. For example, U.S. Pat. No. 4,140,409 to DeVries discloses a package system for containing and dispensing liquids and other flowable materials comprising a reservoir chamber in each half of an elongated package. A prescored fracture line in one surface of the package ruptures when the ends of the package are urged together, and the contents of the chambers are expelled into an applicator sponge that is attached to the outside of the package. However, a disadvantage of packages with such externally placed applicators is that the applicator may become soiled or detached. Also, where a sterile applicator is desired, such a package system may not maintain the applicator under sanitary conditions prior to use.

A covering may be provided to enclose an externally attached applicator. For example, U.S. Pat. No. 4,430,013 to Kaufman discloses a package system that has an interior chamber for containing a fluid, a score line in one surface of the package, and an applicator mounted over the score line. An overwrap with a fracture line on one surface encloses the package and the applicator. When the package is folded in half, the score line is broken and the fluid in the reservoir chamber is expelled into the applicator. The applicator then bursts through the fracture line in the overwrap.

In accordance with this packaging system, the liquid substance is contained and stored within a reservoir separately from the applicator until the package is opened. A drawback of this system is that to dispense the substance from the package, the reservoir chamber must first be opened, and the substance must be ejected therefrom and then dispersed into and through the applicator, which can result in uneven wetting of the applicator. In addition, problems may occur because of premature leakage or evaporation of the liquid contents from the inner chamber of the dispensing package into the external applicator due to a premature break in the fracture line. If the overwrap becomes torn or punctured, the applicator may become uncovered and contaminated, and the liquid substance prematurely dispensed.

To provide a more secure containment, the applicator may be enclosed within a more rigid package. Kaufman also discloses a package system in which an applicator is attached to the inside of a package that has a score line on one surface. The applicator is compressible and sponge-like with a protruding thickened portion placed against the score line. A rib projection is provided on the inside surface of the package opposite the score line to help push the applicator out through the score line when the package is folded. A drawback is that the package cannot be reclosed or resealed with the applicator contained inside once the fracture line is separated and the applicator extruded.

U.S. Pat. No. 4,812,067 to Brown et al. also provides a system that provides separate reservoir chambers in a flexible package. The chambers are compressed to rupture an internal seal in the package which urges the liquid contents into a central dispensing cavity. The ends of the package are bent backward to split open a score line in the surface of the package. Pressure on the package forces the contents to be expelled through the slit in the score line and onto a sponge attached to the outside of the package.

A disadvantage of packaging devices that release their contents by rupturing a score line in the container wall is that flexing of the package prior to use may cause the fracture line to split apart prematurely, thus causing unwanted leakage or premature dispersal of the contents. Conversely, the score line may be constructed such that it is difficult to break.

Therefore, there is a need for a method of dispensing system which addresses the above mentioned problems of prior dispensing systems. In particular, there is a need for a packaging system for dispensing flowable and/or solid substances which has an improved configuration for releasing the contents of the packaging that is not prone to premature rupture, but provides ready dispensing of the package contents. There is also a need for a packaging that is a convenient means of dispensing a plurality of flowable and/or solid substances from multiple chambers within the packaging system, to overcome the physical or chemical incompatibility of the substances, or to allow for sequential application.

SUMMARY OF THE INVENTION

The present invention provides a novel method for containing, dispensing and applying two or more substances such as solids such as powders or granules, and/or flowable substances such as gels, dispersions or solutions.

In one embodiment of the invention there is provided a method for applying a plurality of dermatological agents to the skin from one dispensing and applicator system comprising the steps of (1) providing a dispensing and applicator system comprising a first and second flexible, moisture impermeable cover sheet; a first and second applicator pad each affixed to one surface of said first and second cover sheets, respectively; each of said pads being impregnated with a composition comprising a different dermatological agent; and a flexible, moisture impermeable support sheet having its peripheral surface on its first side releasably sealed to the opposed peripheral surface of the first cover sheet so as to form a first compartment defined by a first continuous seal, and containing the first pad; and said support sheet having its peripheral surface on its second side releasably sealed to the opposed peripheral surface of the second cover sheet so as to form a second compartment defined by a second continuous seal and containing said second pad. The first and second seals are positioned inwardly from the edges of the sheets over a portion of the opposed peripheral surfaces, so as to form a pair of two opposed flanges; (2) sequentially manually grasping and separating each pair of flanges to at least partially release each cover sheet from the support sheet, so that said pads are exposed; and (3) contacting the pads with the skin to release the compositions sequentially from the pads, so as to apply a film of the agents onto the skin.

In another embodiment of the invention there is provided a method for applying a plurality of dermatological agents to the skin from one dispensing and applicator system comprising the steps of: (1) providing a dispensing and applicator system comprising a first and second flexible, moisture impermeable cover sheet; a first and second applicator pad affixed to a first surface of said first and second cover sheets, respectively; each of said pads being impregnated with a first and a second composition, respectively, each composition comprising a different dermatological agent; and a flexible, moisture impermeable support sheet having one peripheral surface releasably sealed to a first opposed peripheral surface of the first cover sheet so as to form a first compartment containing the first pad attached to said first surface of first cover sheet, and said second cover sheet having its first peripheral surface releasably sealed to the opposed second peripheral surface of the first cover sheet so as to form a second compartment containing said second pad attached to said first surface of said second cover sheet, each releasable seal defined by a continuous seal, which seal is positioned inwardly from the edges of the sheets over a portion of the opposed peripheral surfaces, so as to form a pair of two opposed flanges; (2) sequentially manually grasping and separating each pair of the flanges to at least partially release the second cover sheet from the first cover sheet and the first cover sheet from the support sheet, so that said pads are exposed; and (3) contacting the pads with the skin to release the compositions sequentially from the pads, to thereby apply a film of the agents onto the skin.

In still another embodiment of the invention there is provided a method for applying a plurality of dermatological agents to the skin from one dispensing and applicator system comprising the steps of (1) providing a dispensing and applicator system comprising a flexible, moisture impermeable support sheet having a first and a second surface, and having a first applicator pad affixed to the first surface of the support sheet, and a second application pad affixed to the second surface of the support sheet, each of the pads being impregnated with a composition comprising a different dermatological agent in combination with a compatible carrier; wherein the first pad is covered by a flexible, moisture impermeable first cover sheet; and the second pad is covered by a flexible, moisture impermeable second cover sheet, each cover sheet having a peripheral surface releasably sealed to the opposed peripheral surface of the support sheet so as to form a compartment containing a pad and defined by a continuous seal, each seal being positioned inwardly from the edge of the support sheet and the edge of each cover sheet over a portion of the opposed peripheral surfaces, so as to form a pair of two opposed flanges; (2) sequentially manually grasping and separating each pair of flanges to at least partially release each cover sheet from the support sheet, so that the pads are sequentially exposed; and (3) contacting the pads with the skin to release the compositions sequentially from the pad, to thereby apply a film of the agents onto the skin.

For example, the present applicator system is particularly well-adapted to contain, preserve and to sequentially or simultaneously deliver two or more chemically or physically incompatible active ingredients. Preferably, the two-pad applicator will be used to contain, preserve and deliver unit doses of two cosmetic or pharmaceutical ingredients intended for topical application to the skin, e.g., dermatological agents, such as are used to treat a disorder such as acne, dermatitis including atopic dermatitis, insect bites, diaper rash, sunburn, burns, eczema, psoriasis, poison ivy rash, poison oak rash, poison sumac rash, rashes or other skin irritation due to cosmetics, detergents or jewelry and the like.

Novel dispensing and applicator systems are also within the scope of the invention.

As used herein, the term "dermatological agent" includes bioactive substances such as antibiotics and peroxides, as well as compounds intended primarily for cosmetic purposes, such as emollients and sunscreens.

All percentages are by weight unless otherwise indicated.

These and other advantages of the invention over conventional dispensing and application methods will become more apparent after reading the description and claims which follow.

BRIEF DESCRIPTION OF THE DRAWINGS

Throughout the following views, reference numerals will be used on the drawings, and the same reference numerals will be used throughout the several views and in the description to indicate same or like parts of the invention.

FIG. 1 is a perspective view of a first embodiment of the dispensing device of the invention shown in the closed position.

FIG. 2 is a perspective view of a first embodiment of the dispensing device of the invention shown with the first and second cover sheets partially removed.

FIG. 5 is a perspective view of a second embodiment of the dispensing device of the invention shown with the first cover sheet removed and the second cover sheet partially removed.

FIG. 6 is a perspective view of a third embodiment of the dispensing device of the invention shown in the closed position.

FIG. 7 is a perspective view of a third embodiment of the dispensing device of the invention shown with first and second cover sheets removed.

DETAILED DESCRIPTION OF THE INVENTION

Figure 4:
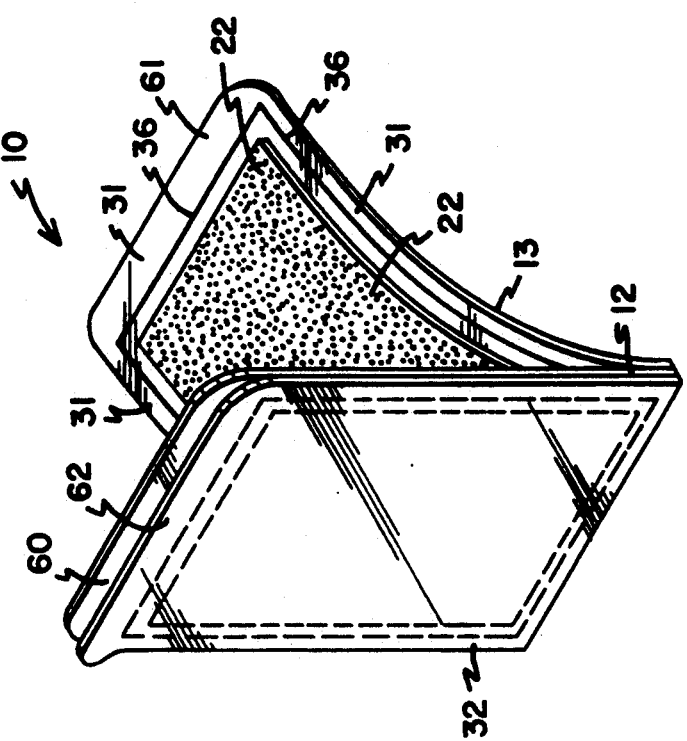
FIG. 4 is a perspective view of a second embodiment of the dispensing device of the invention shown with the first cover sheet partially removed.

Referring now to FIGS. 1 and 2, a first embodiment of the dispensing and applicator device, designated generally by the numeral 10, is shown according to the present invention. The dispensing and applicator device 10 is shown having a first cover sheet 12, a second cover sheet 13 and a support sheet 14. The first and second cover sheets 12, 13 have peripheral surfaces 30, 31 extending completely around the first and second cover sheets 12, 13, respectively. Support sheet 14 has peripheral surfaces 32, 33 extending completely around the first and second surfaces 16, 18 of support sheet 14. Integral with peripheral surfaces 30, 31 of cover sheets 12, 13 are flanges 60, 61 and integral with peripheral surfaces 32, 33 of support sheet 14 is flange 62. Flanges 60, 61 and 62 are used for gripping in order to separate first and second cover sheets 12, 13 from support sheet 14 to open the dispensing and applicator device 10.

Applicator pads 20, 22 are positioned on the surfaces of cover sheets 12, 13 which oppose the surfaces 16, 18 of the support sheet 14. Optionally, recessed areas (not shown) may be provided in cover sheets 12, 13 to receive applicator pads 20, 22. Applicator pads 20, 22 are attached to the surface of cover sheets 12, 13 by known techniques in the art. In order to enclose the applicator pads 20, 22 within the dispensing and applicator device 10, the peripheral edges 30, 31 of first and second cover sheets 12, 13, and peripheral edges 32, 33 of support sheet 14 are releasably sealed together, respectively, in surrounding relation to applicator pads 20, 22, by seal lines 34, 35, thereby defining two compartments within which the applicator pads 20, 22 are enclosed and sealed. Any suitable means of forming real lines 34, 35, such as those discussed below, may be utilized.

The flanges 60, 61 of first and second cover sheets 12, 13 and flange 62 support sheet 14 are created by positioning the seal lines inward from at least a pair of abutting edges of first and second cover sheets 12, 13 and support sheet 14. Flanges 60, 61 provide a means for gripping first and second cover sheets 12, 13 and flange 62 provides a means of gripping support sheet 14 to facilitate the opening of dispensing and applicator device 10 by pulling first and second cover sheets 12, 13 apart from support sheet 14 and thus sequentially or simultaneously exposing applicator pads 20, 22. While these flanges 60, 61, 62 are shown as extending the entire length of one edge of device 10, it is readily apparent that flanges 60, 61, 62 could be provided over a more limited area, such as only at one corner of first and second cover sheets 12, 13 and support sheet 14.

Figure 3:
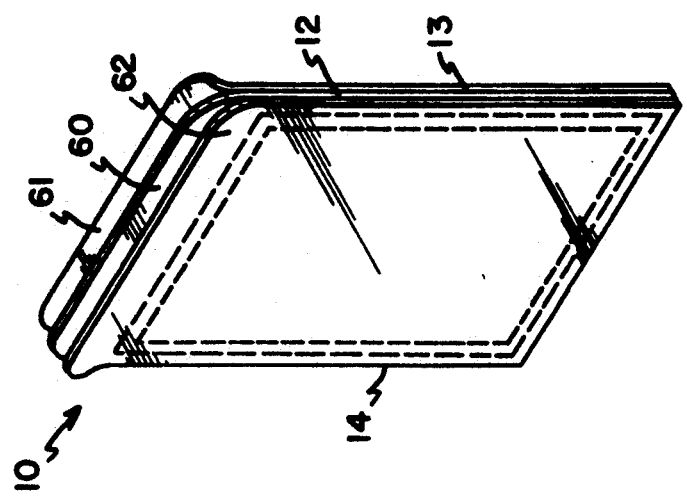
FIG. 3 is a perspective view of a second embodiment of the dispensing device of the invention shown in the closed position.

Referring now to FIGS. 3, 4 and 5, a second embodiment of the dispensing and applicator device, designated generally by the numeral 10, is shown according to the present invention. The dispensing and applicator device 10 is shown having a first cover sheet 12, a second cover sheet 13 and a support sheet 14. The first and second cover sheets 12, 13 have peripheral edges 30, 31 extending completely around the first and second cover sheets 12, 13, respectively. Support sheet 14 has peripheral edge 32 extending completely around support sheet 14. Integral with peripheral edges 30, 31 of cover sheets 12, 13 are flanges 60, 61 and integral with peripheral edge 32, of support sheet 14 is flange 62. Flanges 60, 61 and 62 are used for gripping in order to separate first and second cover sheets 12, 13 from support sheet 14 to open the dispensing and applicator device 10.

First and second applicator pads 20, 22 are on positioned on one surface of first and second cover sheets 12, 13, respectively. Optionally, recessed areas (not shown) may be provided in cover sheets 12, 13 to receive applicator pads 20, 22. Applicator pads 20, 22 are attached to the surface of cover sheets 12, 13 by known techniques in the art. In order to enclose first applicator pad 20, within the dispensing and applicator device 10, peripheral edge 30 on the side of first cover sheet 12 to which first applicator pad 20 is affixed is releasably sealed to opposed peripheral edge 32 of support sheet 14 by means of seal line 34, which is positioned in surrounding relation to first applicator pad 20; thereby defining a compartment within which first applicator pad 20 is enclosed and isolated. In order to enclose second applicator pad 22, within the dispensing and applicator device 10, peripheral edge 31 on the side of second cover sheet 13 to which second applicator pad 22 is affixed is releasably sealed to opposed peripheral edge of the first cover sheet 12 which is opposite to edge 30, by means of seal line 36, which is positioned in surrounding relation to second applicator pad 22; thereby defining a compartment within which second applicator pad 22 is enclosed and isolated. Any suitable means of sealing, such as those discussed below, may be utilized.

The flanges 60, 61 of first and second cover sheets 12, 13 and flange 62 support sheet 14 are created by positioning the seals 37, 36 inward from at least a pair of abutting edges of first and second cover sheets 12, 13 and support sheet 14. Flanges 60, 61 provide a means for gripping first and second cover sheets 12, 13 and flange 62 of provides a means of gripping support sheet 14 to facilitate the opening of dispensing and applicator device 10 by pulling first cover sheet 13 apart form second cover sheet 12, and second cover sheet 12 apart from support sheet 14, thus exposing applicator pads 22, 20, respectively. While these flanges 60, 61, 62 are shown as extending the entire length of one edge of device 10, it is readily apparent that 60, 61, 62 flanges could be provided over a more limited area, such as only at a corner of first and second cover sheets 12, 13 and support sheet 14.

Referring now to FIGS. 6 and 7, a third embodiment of the dispensing and applicator device, designated generally by the numeral 10, is shown according to the present invention. The dispensing and applicator device 10 is shown having a first cover sheet 12, a second cover sheet 13 and a support sheet 14. The first and second cover sheets 12, 13 have peripheral edges 30, 31 extending completely around the first and second cover sheets 12, 13, respectively. Support sheet 14 has first and second peripheral surfaces 32, 33 extending completely around the first and second surfaces of support sheet 14. Integral with peripheral edges 30, 31 of cover sheets 12, 13 are flanges 60, 61 and integral with peripheral edges 32, 33 of support sheet 14 is flange 62. Flanges 60, 61 and 62 are used for gripping for gripping in order to separate first and second cover sheets 12, 13 from support sheet 14 to open the dispensing and applicator device 10.

Applicator pads 20, 22 are on positioned on the opposite surfaces of support sheet 14 by known techniques in the art. In order to enclose the applicator pads 20, 22 within the dispensing and applicator device 10, the peripheral edges 30, 31 of first and second cover sheets 12, 13, and peripheral edges 32, 33 of support sheet 14 are releasably sealed together, respectively, in surrounding relation to applicator pads 20, 22, by seal lines 37, 34, respectively, thereby defining two compartments within which the applicator pads 20, 22 are enclosed and sealed. Any suitable means of sealing, such as those discussed below, may be utilized.

The flanges 60, 61 of first and second cover sheets 12, 13 and flange 62 support sheet 14 are created by positioning the seals 37, 34 inward from at least a pair of abutting edges of first and second cover sheets 12, 13 and support sheet 14. Flanges 60, 61 provide a means for gripping first and second cover sheets 12, 13 and flange 62 provides a means of gripping support sheet 14 to facilitate the opening of dispensing and applicator device 10 by pulling first and second cover sheets 12, 13 apart from support sheet 14 and thus exposing applicator pads 20, 22. While these flanges 60, 61, 62 are shown as extending the entire length of one edge of device 10, it is readily apparent that 60, 61, 62 flanges could be provided over a more limited area, such as only at a corner of first and second cover sheets 12, 13 and support sheet 14.

As depicted in FIGS. 1 through 7, dispensing and applicator device 10 is of a generally rectangular configuration. It will be understood, however, that a variety of shapes and sizes can be accommodated according to the invention.

Applicator pads 20, 22 may be made, for example, of a natural or synthetic, woven or nonwoven fiber, such as gauze, felt, cotton, or from plastic foam or sponge. Other woven or nonwoven material capable of absorbing a liquid or flowable composition may be used. Another applicator useful according to the invention is, for example, a sheet of plastic or stiff paper having pores through which a powder or granular substance, or flowable substance, may be dispensed.

The material used for cover sheets 12, 13 and support sheet 14 should be relatively puncture resistant, non-absorbent, and impermeable, chemically compatible and non-reactive with the flowable substance or material contained in the dispensing and applicator device 10 to prevent leakage or migration of the contents out of the dispensing and applicator device 10, and substantially impermeable to external contaminants such as air, dust, liquids and the like.

Suitable materials for cover sheets 12, 13 and support sheet 14 should be materials capable of allowing cover sheets 12, 13 to be sealed to support sheet 14 along the seal lines in order to form a containing and dispensing package that does not separate during normal use. For example, cover sheets 12, 13 and support sheet 14 may be made of a thermoplastic and heat sealable polymeric film material, such as polyethylene, polyvinyl chloride, or polyamide-type resins, according to known techniques in the art. Such a film may be used alone or adhered to a non-heat sealable material by known techniques. Cover sheets 12, 13 and support sheet 14 may be formed, for example, of glassine paper, cellophane, polyethylene, polypropylene, polyvinyl chloride, polyester, nylon and the like. Cover sheets 12, 13 and support sheet 14 may also be formed of an aluminum foil that is coated or sealed with a thermoplastic material such as a polyethylene, polyester, polyvinyl resin or cellulose acetate. Alternatively, the foil may comprise a cellulosic material lined with a thermoplastic film or other synthetic or plastic material. A foil-lined paper board may also be used. For examples of flexible materials suitable for cover sheets 12, 13 and support sheet 14, see for example, "Coatings and Laminations," in *Handbook of Package Engineering* (2d ed.), pages 4-1 to 4-20, J. F. Hanlon, the disclosure of which is incorporated by reference herein.

Cover sheets 12, 13 and support sheet 14 may also be formed of a laminate or covered with a lamination that includes components such as fluorohalocarbon (Aclar), cellulose acetate, cellophane, polyester, polyvinyl chloride (PVC), polyethylene (PE), polypropylene, rubber hydrochloride, PVDC, and the like. A laminated cover sheets 12, 13 and support sheet 14 may include, for example, paper or foil with polyester, acetate with foil and lacquer, acetate with metallized Mylar and polyester, and other suitable combinations that will provide, for example, a stiff yet flexible cover sheets 12, 13 and support sheet 14, a moisture or gas barrier, protection of the contents from photochemical change from exposure to light, prevention of plasticizers and stabilizers from the film by the contents of the package, and other like factors. For example, cover sheets 12, 13 and support sheet 14 may be formed of a laminated paper board material such as a stiff cardboard that is covered with a foil material and/or a structured film. The layers of the lamination may be sealed together, as for example, by heat.

A coating to provide a nonporous gas and/or vapor barrier, as for example polyethylene and/or polyester, may be applied to the outer surface of cover sheets 12, 13 and support sheet 14. The coating may provide a sealant to prevent entry of vapors or water, or evaporation of the contents from dispensing and applicator device 10, such as an organic solvent vehicle. Cover sheets 12, 13 and support sheet 14 may be coated, for example, with a wax coating such as a paraffin wax alone or as part of a blend, as for example, with microcrystalline wax and polyethylene; a varnish coating; a polyvinylidene chloride (PVDC) coating; a polyester (PET) coating, as for example, polyethylene terephtalate; a heat seal coating, as for example, with polyethylene, vinyl, acetate, polyvinyl resin or cellulose acetate, or other cellulosics, or polyvinyl chloride; an extrusion coating, as for example, with polyethylene; or a metallized film coating, as for example, a metallized polyester, nylon, polyethylene, or polypropylene having a thin layer of aluminum. A coextruded or composite film may also be used to cover sheets 12, 13 and support sheet 14. A composite film may include, for example, polyethylene and polypropylene with nylon, EVA, saran, and/or styrene.

As stated above, support sheet 14 may be made of the same or similar material as that used for cover sheets 12, 13, but preferably support sheet 14 is somewhat more rigid than cover sheets 12, 13. For example, support sheet 14 may additionally be made of synthetic organic polymeric sheet material such as polystyrene, acrilonitride or acrylic copolymer with polystyrene, for example by extrusion, thermoforming, vacuum-forming, or other technique known in the art. A coating to provide a nonporous gas and/or vapor barrier, as for example, a coating, a co-extruded plastic such as polyethylene and polyethylene terephtalate, or a laminate of these materials and others such as polypropylene, polyvinylidene chloride, cellophane, and the like, may be applied to the outer surface of support sheet 14 as a sealant to prevent entry of vapors or water, or evaporation of the contents of dispensing and applicator device 10, such as an organic solvent.

Cover sheets 12, 13 may be sealed to support sheet 14 by a heat seal, pressure seal, high frequency seal, ultrasonic seal, a crimp, a bonding material or by means of various adhesive materials. Other suitable attachment methods or means may be used to effect a secure seal according to known techniques in the art. For example, heat may be applied according to known techniques in the art to cause a bonding of the thermoplastic liner of support sheet 14 to cover sheets 12, 13. A temporary heat seal may be formed by applying relatively narrow lines of heat seal, and wider lines of heat seal may be applied to effect a more permanent seal. A permanent seal may also be provided by applying a high degree of heat using an appropriately high temperature, and a lower degree of heat using a lower temperature to provide a temporary seal.

Adhesives used to form the seal lines should be nonreactive and compatible with the materials used for cover sheets 12, 13 and support sheet 14 as well as with the contents within the compartment or subcompartments of dispensing and applicator device 10, and should not permit premature leakage or diffusion of such materials from the package. An example of adhesives for effecting a releasable seal include, for example, polyvinyl chloride (PVC) applied to one surface, and polyvinyl acetate applied to a second surface. Cover sheets 12, 13 and support sheet 14 may also be sealed together by a piece of material (not shown) attached between cover sheets 12, 13 and support sheet 14.

It is understood according to the invention that applicator pads 20, 22 may each contain the same or different substances. Advantageously, the dispensing and applicator device 10 of the invention may be used to dispense two or more substances that should be, or are preferably, kept separated until the desired application. The two components would then be dispensed according to the invention simultaneously by the two applicator pads 20, 22, or sequentially from one of the applicator pads 20, 22 at a time. A wide variety of different cosmetic or bioactive agents as those combinations set forth herein, may be impregnated in applicator pads 20, 22.

Acne

Acne is a common inflammatory disease of human skin, and concentrates in skin areas where sebaceous glands are largest, most numerous, and most active. In its milder types, it is a more or less superficial disorder which is evidenced by slight, spotty irritations and ordinary skin hygiene is a satisfactory treatment. However, in the more inflammatory types of acne, bacterial invasion of or about the pilosebaceous follicles occurs and pustules, infected cysts and, in extreme cases, canalizing inflamed and infected sacs appear. These lesions may become extensive and leave permanent, disfiguring scars.

To reduce the severity of acne, various forms of medication have previously been topically applied to the skin. Antibacterial soaps have been used as well as bactericidal agents such as sulfur and resorcinol. Other topical compositions have separately contained benzoyl peroxide, hexachlorophene, erythromycin or neomycin sulfate. None of these prior preparations has been completely effective.

As disclosed by Klein et al. (U.S. Pat. No. 4,497,794), it was discovered that a mixture on the skin of a peroxide, especially benzoyl peroxide and an antibiotic or antibacterial such as clindamycin, neomycin, sodium sulfacetamide, sulfur, tetracycline or erythromycin is particularly beneficial as they can exert a statistically significant synergistic effect. Peroxides inhibit the formation of free fatty acids in the skin, primarily through inactivation of extracellular lipase (via oxidation) necessary to cleave triglycerides into free fatty acids and glycerol. The antibiotic or antibacterial component reduces the concentration of *Corynebacterium acnes* (i.e., P. acnes), a normal anaerobic bacteria which is the prime source of the lipase. Instead of the benzoyl peroxide, which is preferred, peroxides such as stabilized hydrogen peroxide and peroxides of organic acids, such as a lauroyl peroxide, may be used.

As disclosed by Klein et al., erythromycin and benzoyl peroxide may be applied to the skin in combination in a preformulated aqueous-alcoholic gel. However, if a mixture is first made up and then applied to the skin, it is best that the mixture be made at the time of application or that the mixture be used within twenty-four hours. The prompt use of a premix is necessary due to the chemical incompatibility of the two active agents. Because of this, it is advisable that the two agents be put in separate vials, bottles or other containers. For example, the Klein et al. patent discloses a kit containing, separately bottled liquid compositions comprising 5% benzoyl peroxide and a solution of erythromycin in ethanol or acetone.

However, separately packaging multiple dosages of the two active ingredients presents a number of disadvantages to the end-user. For example, a unit application dosage of each active must be removed sequentially from each container and absorbed onto an applicator, such as a cotton swab, so that it can be coated onto the skin of the user. This provides opportunities for spillage or over- or under-dosing, which can lead to skin irritation and other side effects. Furthermore, such a multidose system necessarily adds to the costs of packaging, shipping and storage.

As can readily be ascertained from the foregoing description, the dispensing and applicator system is intended to overcome these difficulties. As exemplified, the present dual-pad package can readily contain, preserve and deliver single unit doses of two or more chemically- or physically-incompatible active ingredients. For example, an antibiotic in combination with a liquid, semi-liquid (cream) or gelled aqueous or non-aqueous vehicle can be absorbed by and retained by the first pad and a second ingredient which is physically- or chemically-incompatible with the antibiotic, such as a peroxide, can be absorbed and retained by the second pad, preferably in combination with the appropriate vehicle.

Alternatively, the present application system can be used to contain and release two active ingredients which are desirably applied sequentially, whether or not they are physically or chemically compatible on the skin. Other examples of pairs of such ingredients include (a) an antibiotic or peroxide for treatment of a skin disorder and a keratolytic/antiseptic agent such as salicylic acid; (b) retinoic acid (Retin ® A) and moisturizing agent to counteract the drying/scaling effects of the Retin ® A, and/or a sunscreen to protect the skin against the increased sensitivity to the sun caused by the Retin ® A, (c) a pigmented, wax-based make-up composition, such as eye-shadow, blush, foundation bases and the like, or a sunscreen in a similar water-insoluble vehicle; and liquid make-up remover formulations that are formulated to remove the make-up or the sunscreen; and (d) a steroid, preferably a corticosteroid and a complementary dermatological agent, such as an antihistamine, antifungal, antibiotic and/or sunscreen.

As can be readily seen from the figures, the present applicator is adapted to sequentially release and produce in situ a mixture of two (or more) active ingredients on the target skin area to be treated. Both cover sheets can be removed, and the attached pads can be sequentially applied to the skin area to be treated. Alternatively, the covering sheets can be removed to expose the applicator pads, as it is desired to apply the active therefrom, e.g., at substantial intervals of time and to different areas of the skin, while leaving the remaining pad or pads enclosed.

Although each pad will contain at least one active ingredient, preferably in combination with a suitable carrier vehicle, compositions containing multiple active, chemically compatible ingredients can be absorbed onto each of one or more of the pads.

COMPOSITIONS FOR ACNE TREATMENT

I. Peroxide

One pad in the present acne-treatment applicator system will preferably comprise an effective fatty-acid-inhibiting amount of a peroxide, i.e., hydrogen peroxide or an organic peroxide, preferably in combination with a gelled or semiliquid (lotion or cream) vehicle.

No matter what vehicle is employed, on a weight basis, the selected antibiotic (clindamycin, tetracycline and/or erythromycin) and the selected peroxide should be measured out so that as applied to the skin, the latter is from about one to about thirty times the weight of the former, preferably from about one to about five times. Thus, on the first pad, the selected antibiotic should be present at a level ranging from 0.5% to 5.0% w/w of the total composition absorbed into the pad and, on the second pad, the selected peroxide should be present at a level ranging from 1.0% to 30% w/w of the total composition absorbed into the pad. A preferred concentration is about 2% to about 3% of the selected antibiotic and about 5% to about 10% of the selected peroxide, based on the total weight of each of the compositions which are used to impregnate the pads.

1. Aqueous Emollient Peroxide-Containing Gels

A preferred peroxide-containing composition for use on one of the pads of the present applicator system comprises an effective anti-acne amount (about 1-10%, preferably about 2.5-7.5%) of an organic peroxide, preferably benzoyl peroxide in combination with an aqueous gel comprising water (about 40-75%), an effective amount (about 0.25- 5%) of an inorganic gelling agent, an inorganic emollient oil plus an emollient organic ester (2.5-10%) and, optionally, an amphoteric surfactant (0.025-0.25%) and a watermiscible organic solvent, i.e., 10-20% of a ($C_2$-$C_4$) alkanol.

a. Emollient Oils

Useful emollient oils for incorporation into the aqueous reactant phase include those water-insoluble liquids which can function to soften the skin of the user and provide a degree of barrier protection against environmental irritants.

Preferred emollients oils for use in the present invention include mixtures of (i) inorganic emollient oils (minerals or silicone oils) with (ii) emollient organic esters. Mineral oils are complex mixtures of paraffin and naphthalene hydrocarbons, e.g., the $C_{18}-C_{36}$ hydrocarbon mixtures available from Penreco, Butler, PA, e.g., Peneteck ® technical mineral oil (viscosity 3.4–4.7 centistokes @40° C.), the Drakeol ® light mineral oils, USP (viscosities 6.5–30.2 centistokes @40° C.) and the Drakeol ® mineral oils, USP (viscosities 35.0–70.0 @40° C.). The specific gravity of mineral oils useful in the practice of the present invention preferably is about 0.80–0.9 at 15.6° C. (60° F.). Preferred mineral oils for use in the present vehicles are odorless, colorless (30+Saybolt color) and comply with FDA requirements under the Federal Food, Drug and Cosmetic Act.

Silicone fluids can also be used alone or in combination with the mineral oil component. Useful classes of silicone fluids include the linear polydimethylsiloxanes or the tetrameric or pentameric cyclic siloxanes (cyclomethicones) which are available from Rhone-Poulenc, Inc. (Monmouth Junction, N.J.) as the Rhodorsil ® fluid series in a wide range of viscosities (i.e., 10–10,000 cps.). Fluids of about 0.5–150 cps viscosity, preferably about 25–100 cps, are preferred. Preferably, mineral oil and/or silicone oils will make up about 0.1–1% of the peroxide-containing gelled vehicle.

Preferred emollient esters include those organic esters that can also function as nonionic surfactants. They include about 0.5–5% of (polyoxyethylene) (($C_8-C_{12}$) fatty acid) esters of glycerol, such as PEG-7 glyceryl cocoate (Cetiol ® HE, Henkel), PEG-30 glyceryl cocoate, PEG-12 glyceryl laurate, PEG-20 glyceryl oleate, and the like, wherein the number designates the approximate number of oxyethylene moieties present.

Another preferred class of emollient ethers are the polyoxypropylene, polyoxyethylene ethers of lanolin or of ($C_8-C_{22}$) fatty alcohols, such as PP5-5-Ceteth-20 which is the ether of cetyl alcohol having 20 ethylenoxy units and 5 propylenoxy units (Procetyl ® AWS, Croda), and Lanexol ® AWS (PPG-12-PEG-50 lanolin, Croda). These mixed polyalkylenoxy ethers may be present at about 0.1–0.5% of the total peroxide-containing gelled vehicle.

Other useful emollient esters include ($C_5-C_{30}$)-alkyl, ($C_8-C_{22}$)fatty acid esters, wherein the fatty acid moiety is optionally substituted with a ($C_8-C_{22}$)alkanoyl group. Such esters are commercially available, e.g., as Ceraphyll ® 847 [2-octyl(dodecyl)] (12-steroyl-stearate), Ceraphyll ® 368 (2-ethylhexylpalmitate) and Ceraphyll ® 230 (isocetyl stearate) from Van Dyk & Co., Belleville, N.J. Preferably, the aqueous reactant phase will include about 5–50% by weight of these fatty acid esters, most preferably about 10–45%.

Other useful classes of water-insoluble emollient esters include the ($C_8-C_{22}$)fatty acid esters of propylene glycol, e.g., propylene glycol dicaprylate/dicaprate (Edenol ® 302); the ($C_6-C_{12}$)fatty alcohol esters of hydroxy ($C_8-C_{22}$)fatty acids, e.g., octylhydroxy stearate (Naturechem ® DHS); the esters of fatty alcohol(polyethylene oxideethers) with fatty acids, e.g., myreth-3-caprate, myreth-3-myristate and myeth-3-myristate (Cetiol ® 1414-E, Henkel), wherein the number indicates the number of oxyethylene moieties present; the benzyl alcohol esters of one or more $C_{10}-C_{20}$ fatty acids, e.g., benzyl linoleate (Dermol ® 618, Alzo, Inc., Matawan, N.J.); the fatty alcohol esters of benzoic acids such as the $C_{12}-C_{15}$ alkylbenzoates (Finsolv ® TN, Finetex, Inc.) described in U.S. Pat. Nos. 4,278,655 and 4,275,222; the liquid fatty alcohol esters of $C_3-C_6$ aliphatic carboxylic acids, i.e., isodecyl neopentanoate (Dermol ® 105); and the ($C_1-C_5$)alkanol di- or triesters of dimer or trimer acid (the dimer or trimer of oleic acid). Such esters are commercially available as Schercemol ® TT (triisopropyl trimerate) and Schercemol ® DID (diisopropyl dimerate, Scher Chemicals, Clifton, N.J.). The liquid fatty acid-esters of dimer acid may also be successfully employed in the present compositions, e.g., the diisostearyl ester of dimer acid, Schercemol ® DISD.

b. Surfactant

Surfactants may also be used to stabilize the gelled composition. A preferred class of these materials is fatty acid amides such as the mono- and dialkanolamides of $C_8-C_{22}$ fatty aids, e.g., a mono- or di($C_2-C_4$)alkanolamide. Commercially available, nonionic surfactants of this class include lauramide DEA (Standamid TM LP, Henkel), lauramide MEA (Monamid TM LMA, Mona), lauramide MIPA (Monamid TM LIPA, Mona), myrisamide MEA, myristamide MIPA, Myristamide DEA, Oleamide DEA, oleamide MEA, oleamide MIPA, cocamide MEA, cocamide DEA, cocamide MIPA, stearamide MEA, stearamide MIPA, stear-amide DEA and the like.

Other useful nonionic surfactants include the amine oxides, such as the $C_{10}-C_{20}$-alkyl-di(lower)alkyl-amine oxides or the [$C_{10}-C_{20}$-alkylamido, ($C_2-C_5$)alkyl]di(lower)-alkyl-amine oxides. Especially preferred members of this class include lauryl(dimethyl) amine oxide, myristyl(dimethyl)amine oxide, stearyl(dimethyl)amine oxide (Schercamox TM DMS, Scher Chemicals, Inc., Clifton, N.J.); coco(bishydroxyethyl)amine oxide (Schercamox TM CMS), tallow(bishydroxyethyl)amine oxide and cocoamidopropyl(dimethyl)amine oxide (Schercamox ® C-AA).

A further useful class of surfactants is the anionic surfactants, including the $C_{14}-C_{18}$ primary alkyl sulfates, such as sodium lauryl sulfate, sodium cetyl sulfate and sodium stearyl sulfate.

c. Gelling Agents

The present peroxide-containing vehicles will comprise an amount of an inorganic or organic gelling agent effective to gel or thicken the aqueous-alcoholic mixture to at least a cream- or lotion-like consistency.

Preferably, the inorganic gelling agents employed will comprise those of natural or synthetic of mineral origin. Preferred gelling agents are the montomorillonite clays such as the saponites, hectorites, laponites and the montmorillonite colloidal clays such as Veegum TM (Vanderbilt Minerals, Murray, Ky.) or Magnabrite TM (American Celloid Co., Skokie, Ill.. Clay-based gellants containing montmorillonite and aluminum hydrosilicate together with suborganic radicals are available as the Tixogel TM series (United Catalysts, Louisville, Ky.). A useful montmorillonite clay gelling agent is a bentonite such as Korthix TM H (Kaopolite, Inc., Union, N.J.). Inosilicates can also be used, alone or in combination, with the clays. Preferred inosilicates are the naturally-occurring calcium metasilicates such as wollastonite, available as the NYAD TM wollastonite series (Processed Minerals Inc., Willsboro, N.Y.). Synthetic sodium magnesium silicate clays, alumina, magnesium aluminum silicate, and fumed silicas can also be used as gelling agents.

Useful organic gelling agents include microcrystalline cellulose and hydroxyalkyl cellulose ethers such as hydroxypropylmethyl cellulose (HPMC), hydroxymethyl cellulose (HMC), carboxymethyl cellulose (CMC), 2-hydroxyethyl cellulose, 2-hydroxyethylmethyl cellulose, and 2-hydroxypropyl cellulose (Klucel ® H).

Organic gelling agents useful in the practice of the present invention also include polyvinylpyrrolidone and polymeric organic waxes. The useful polymeric waxes include ethylene acrylate copolymers, ethylene acrylic acid copolymers and polyethylene (e.g., oxidized polyethylenes). These materials are commercially available in the form of aqueous emulsions or dispersions, e.g., from Allied Chemical, Morristown, N.J., as the A-C Copolymer and A-C Polyethylene series, such as A-C Copolymer 540, A-C Copolymer 580 and A-C Polyethylene 617 and 629. Waxy polyethylene glycols (PEG) such as those of a molecular weight of about 800 to 1700-2000 are preferred for use in the present gels.

Preferred gelling agents include the so-called hydroxylated vinylic polymers, particularly those disclosed in U.S. Pat. No. 2,798,053. Among those hydroxylated vinylic polymers of special interest herein are described generally as interpolymers of a monomeric monoolefinic acrylic acid, and from about 0.1% to about 10% by weight based on the total monomer of a monomeric polyether of an oligosaccharide in which the hydroxyl groups which are modified are esterified with allyl groups with said polyether containing at least two allyl ether groups per oligosaccharide molecule. Commercially available interpolymers of this type are marketed under the trade name Carbopols ®. These are described as being polymers of acrylic acid crosslined with about 1% of a polyallyl ether of sucrose having an average of 5.8 allyl groups for each sucrose molecule. These polymers have molecular weight in the order of magnitude of 1,000,000. Such polymers are available from the B. F. Goodrich Chemical Company and are sold under such trademarks as Carbopol ® 934, Carbopol ® 940, Carbopol ® 941 and Carbopol ® 934P.

The quantity of gelling agent that may be contained in the present compositions may also vary somewhat. Ordinarily, this will constitute about 0.1% to about 15% by weight, and preferably about 0.5% to about 3% by weight, based on the total weight of the finished peroxide-containing vehicle.

A typical formulation for an aqueous-alcohol emollient benzoyl peroxide gel is given on Table I, below. The gel contains 15% isopropanol and 5% benzoyl peroxide, and has the consistency of a light gel.

TABLE I

| INGREDIENTS | CTFA CHEMICAL NAME* | % |
|---|---|---|
| Water, distilled | — | 63.73 |
| Laponite XLS | Sodium Lithium Magnesium Silicate | 1.97 |
| Isopropanol | Isopropyl Alcohol | 15.00 |
| Cetiol HE | PEG-7 Glyceryl Cocoate | 1.45 |
| Edenol 302 | Propylene Glycol Dicaprylate/Dicaprate | .43 |
| Schercemol DISD | Diisostearyl Dilinoleate | .65 |
| Naturechem OHS | Octyl Hydroxystearate | .95 |
| Finsolv TN | C12-15 Alcohols Benzoate | .70 |
| Cetiol 1414-E | Myreth-3 Myristate | .16 |
| Lamapon S | Potassium Coco-Hydrolyzed Animal Protein | .05 |

TABLE I-continued

| INGREDIENTS | CTFA CHEMICAL NAME* | % |
|---|---|---|
| Procetyl AWS | PPG-5-Ceteth-20 | .15 |
| Lanexol AWS | PPG-12-PEG-50 Lanolin | .15 |
| Mineral Oil Light | Mineral Oil | .25 |
| Schercamox C-AA | Cocamidopropylamine Oxide | .06 |
| Benzoyl Peroxide (35%) | — | 14.30 |
| | | 100.00 |

*See CTFA Cosmetic Ingredient Dictionary, N. F. Estrin, ed., The Cosmetic, Toiletry and Fragrance Association, Inc., pub., Washington, D.C. (3d ed. 1982).

To prepare this formulation, the laponite is added to the water with vigorous stirring. In another vessel, the emollient oils and the amine oxide are added in the order listed with stirring, and the mixture is heated gradually to 60° C., then cooled to 25° C. The isopropanol is then added to the water-laponite stirring with good agitation, and the resultant mixture is stirred into the emollient mixture, followed by the addition of benzoyl peroxide.

2. Aqueous, Non-Emollient Peroxide Gels

The complex mixture of emollient esters and surfactants listed on Table I is not essential to the preparation of an aqueous benzoyl peroxide-containing acne treatment gel. For example, 10–20% benzoyl peroxide can be stably dispersed in about 50–80% water with the aid of an effective amount of one or more inorganic gelling agents, e.g., 1–3, such as those useful to prepare the emollient gels above. Preferably, about 0.5–25%, most preferably about 2–20% of total gelling agent will be used. Typical formulations for four such gels are provided in Table II, below.

TABLE II

| INGREDIENTS | CTFA CHEMICAL NAME | Formulation | | | |
|---|---|---|---|---|---|
| | | A % | B % | C % | D % |
| Water | — | 66.50 | 83.13 | 83.38 | 73.04 |
| Laponite XLS | Sodium Lithium Magnesium Silicate | 2.06 | — | — | 1.80 |
| Laponite XLG | Sodium Lithium Magnesium Silicate | — | 2.57 | 1.81 | .46 |
| Veegum HV | Magnesium Aluminum Silicate | — | — | 0.51 | — |
| Dispal Alumina 23N4-20 Sol. | Aluminum Oxide Dispersion | 17.14 | — | — | — |
| Dispal Alumina 23N4-80 Powder | Aluminum Oxide | — | — | — | 10.40 |
| Benzoyl Peroxide (35%) | — | 14.30 | 14.30 | 14.30 | 14.30 |
| Total | | 100.00 | 100.00 | 100.00 | 100.00 |

Gels A, B and D are thick/viscous gels. Gel C is thixotropic, in that it fluidizes when subjected to shear.

3. Anhydrous Emollient Peroxide Gel

The benzoyl peroxide gel component of the present invention can also be prepared by dispersing the benzoyl peroxide in an essentially water-alcohol free blend of surfactants, along with about 1–10% of the inorganic gelling agent. Such gels can comprise about 75–90% of a mixture of inorganic and organic emollient oils, about 1–10% peroxide and, optionally, above 0.1–1% of amine oxide or other amphoteric surfactant. The inorganic oil is preferably a minor proportion, i.e., about 1-7.5% of the finished gel. A typical formulation for such a gel is given in Table III below.

TABLE III

| INGREDIENTS | CTFA CHEMICAL NAME* | % |
|---|---|---|
| Cetiol HE | PEG-7 Glyceryl Cocoate | 23.64 |
| Edenol 302 | Propylene Glycol Dicaprylate/Dicaprate | 7.01 |
| Schercemol DISD | Diisostearyl Dilinoleate | 10.51 |
| Naturechem OHS | Octyl Hydroxystearate | 15.49 |
| Finsolv TN | C12-15 Alcohols Benzoate | 12.80 |
| Cetiol 1414-E | Myreth-3 Myristate | 2.61 |
| Lamapon S | Potassium Coco-Hydrolyzed Animal Protein | 0.81 |
| Procetyl AWS | PPG-5-Ceteth-20 | 4.07 |
| Mineral Oil Light | Mineral Oil | 4.07 |
| Schercamox C-AA | Cocamidopropylamine Oxide | 0.49 |
| Cabosil M-5 | Amorphous Silica | 4.20 |
| Benzoyl Peroxide (35%) | — | 14.30 |
| Total | | 100.00 |

These gels are "anhydrous" in the sense that the only water or alcohol present is provided via the commercially available forms of the emollient esters and surfactants, and is preferably ≦5% of the total gel.

II. Antibiotic

Preferred dual pad applicators intended for acne treatment will comprise a pad having an absorbed aqueous, alcoholic, or aqueous-alcoholic solution of the antibiotic, of which erythromycin, tetracycline, clindamycin and the pharmaceutically acceptable salts thereof are preferred. Useful salts include the salts of inorganic or organic acids, such as the hydrochloride, phosphate, glyconate, citrate, maleate, stearate, and hydrobromide salts. Useful alcohols include ethanol, isopropanol and mixtures thereof. Benzyl alcohol and/or butanol can also be used in combination with varying amounts of water. All, or a part of the alcohol, can be replaced by other volatile water-miscible organic solvents such as propylene glycol, m-pyrol, liquid polyethylene glycols, acetone, THFA and the like.

The antibiotic or salt thereof will preferably be dissolved or dispersed in the solvent or solvent system at a concentration effective to significantly decrease the skin concentration of *Corynebacterium acnes* upon topical application of about 0.5-5.0 mls of the antibiotic solution for the skin of the afflicted human or animal, e.g., an about 0.5%-5% solution or dispersion of the antibiotic in the solvent or solvent system is preferred.

Emollient organic esters are preferably also self-emulsified into an aqueous alcohol system, e.g., one comprising about 80-95% aqueous alcohol, about 5-15% emollient organic ester, and about 0.1-5% antibiotic, in order to provide the pad with a better skin-feel and to aid in the even distribution of the antibiotic on the skin. A typical emollient formulation comprising 1.0% clindamycin phosphate, is given on Table IV, below.

TABLE IV

| Ingredient | Percent |
|---|---|
| Water | 20.0 |
| Isopropanol | 70.3 |
| 10% NaOH | 0.7 |
| Clindamycin phosphate | 1.0 |
| Emollient Esters | |
| Cetiol HE | 2.3 |

TABLE IV-continued

| Ingredient | Percent |
|---|---|
| Myritol 318* | 0.7 |
| Naturechem GTR** | 1.5 |
| Finsolv TN | 2.8 |
| Cetiol 144-E | 0.3 |
| Procetyl AWS | 0.5 |

*Caprylic/Capric Triglyceride
**Glyceryl triacetyl ricinoleate

To prepare this formulation, clindamycin phosphate is dissolved in the water at 25° C. and isopropyl alcohol added, this solution is added to a preformed blend of the emollient esters and the pH of the mixture is adjusted to 6.8 with 10% NaOH.

Erythromycin can replace clindamycin in this formulation.

III. Salicylic Acid

In dual pad applicator packs intended for acne treatment, the antibiotic or benzoyl peroxide composition can be replaced with a composition containing salicylic acid, which acts as an antiseptic, an antifungal and a topical keratolytic agent. A suitable vehicle for salicylic acid can be prepared by mixing water with a gelling agent and adding a water-miscible organic solvent in a weight ratio of about 0.1-4 parts water to 1.0 part solvent, e.g., a ($C_2$-$C_4$)-alkanol. The salicylic acid is dispersed in this mixture at about 0.5-10% of the finished composition. Two typical salicylic acid formulations are given on Table V, below.

TABLE V

| Ingredients | CTFA Chemical Name | A % | B % |
|---|---|---|---|
| Water, distilled | — | 74.57 | 12.62 |
| Klucel H | Hydroxypropylcellulose | 1.52 | — |
| Carbopol 934P NF | Carbomer 934P | — | 1.95 |
| Isopropanol | Isopropyl Alcohol | 21.74 | 82.52 |
| Salicylic Acid Powder U.S.P. | — | 2.17 | 2.91 |
| Total | | 100.00 | 100.00 |

Formulation B yielded a light, fluid gel that spread into an even film. Formulation A yielded a thicker, fluid gel.

IV. Retinoic Acid

As disclosed hereinabove, for the topical treatment of acne using the present dispensing an applicator system, one of the pads can be impregnated with a liquid, semi-liquid or gelled formulated comprising an effective anti-acne amount of retinoic acid, while the other pad or pads preferably contain an emollient composition to counteract the drying/scaling properties of the retinoic acid, and/or an effective amount of a sunscreen composition to protect the user from retinoic acid-induced sensitivity to UV light.

Useful retinoic acid compositions can be formulated as creams, gels, or liquids; preferably comprising about 0.01-0.25 wt-% of retinoic acid. Useful gels can be formed in aqueous, water-miscible organic solvent vehicles comprising water:solvent ratios of about 9:1 to 1:9, in combination with an effective amount of an organic and/or inorganic gelling agent, of the classes described hereinabove. Retinoic acid-containing liquids can simply be prepared by dissolving an effective amount of retinoic acid in water organic solvent, using nontoxic organic solvents, such as the ($C_2$-$C_4$)alkanols and liquid polyoxyethylene glycols disclosed hereinabove. Due to the unstable nature of retinoic acid, minor but effective amounts of anti-oxidants, such as BHT, are preferably included in these formulations.

V. Skin Moisturizing Composition/Sunscreens

Emollient compositions which soften and protect the skin are preferably used in conjunction with a dermatological composition comprising retinoic acid, or as a carrier vehicle for retinoic acid. When used in conjunction with retinoic acid, the emollient compositions preferably include an effective amount, i.e., 1–10 wt-% of one or more, i.e., 1–3 sunscreen compounds. These include oxybenzone, ethyldihydroxypropyl-p-amino benzoate, octyl dimethyl-p-aminobenzoate, para-aminobenzoic acid, and the like. Useful emollient compositions include those disclosed in Smith et al. (U.S. Pat. No. 4,559,157) which are oil-in-water emulsions comprising an oil phase containing at least one emollient oil and at least one emollient wax stabilizer, dispersed in an aqueous phase comprising at least one polyhydric alcohol emollient and at least one amphoteric (amine oxide) or anionic surfactant. Effective amounts of bactericidal preservatives and fragrance may also be employed in the impregnating emulsion. These emulsions are formulated so that an effective amount of emollients and fragrance is released and evenly coated onto the skin with no "skipping" or separation when the impregnated pad is pressed or rubbed against a moist skin surface. This requires that the emulsion be formulated so that it will be stable and not break when mixed with the additional water present on the skin due to bathing, showering or the like.

It has been found that emollient emulsions stable under these conditions can be formulated by dispersing an oil phase comprising one or more emollient oils and one or more emollient wax stabilizers in an aqueous phase comprising one or more polyhydric alcohol emollients and one or more water-soluble organic surfactants.

Therefore, the emulsions of the present invention preferably will comprise about 15–50% of water-insoluble or soluble active ingredients, i.e., the emollients, surfactants, fragrance and preservatives; and 50–85% water, preferably distilled or deionized water. About 7–20% of the active ingredients will be present as the oil phase of the emulsion, while the remainder of the active ingredients will be fully soluble in the water phase. Emollients will preferably comprise about 10–50% by weight of the emulsions. Emollients useful in the practice of the present invention are generally described by G. Barnet, Emollient Creams and Lotions, and by S. J. Strianze, Hand Creams and Lotions, in *Cosmetics--Science and Technology*, Wiley Interscience Pub. (1957) at pages 99–181.

A. Emollient Wax Stabilizer

The emollient oils useful in these compositions have been described hereinabove. Emollient wax stabilizers are waxy solids at room temperature. They function to soften and smooth the skin surface and to prevent evaporation of interior skin moisture. They also can function as nonionic emulsifying agents and act to adjust the final viscosity of the composition. The emollient wax stabilizers useful in the practice of the present invention include beeswax, spermaceti, solid hydrocarbons, $C_{12}$–$C_{18}$ fatty alcohols, glyceryl monostearate, ethylene glycol monostearate, polyethylene glycol distearate and other ($C_{12}$–$C_{18}$)fatty acid-($C_2$–$C_5$) polyol esters. Particularly useful in the practice of the present invention are the fatty alcohols, such as lauryl, cetyl, oleyl and stearyl alcohols or mixtures thereof, and the fatty acid-polyol esters, i.e., glyceryl monostearate, which is commercially available as Cerasynt ® Q from Van Dyk & Co., Belleville, N.J. In one class of emulsions useful in the practice of the present invention, all or a part of the emollient oil, isostearyl neopentanoate, or Ceraphyll ® 375, is replaced with one of the emollient waxes of the Softisan ® Series (Dynamit Nobel Chemicals, Rockleigh, N.J.), a fragrant emollient ester of the class of compounds designated as triglycerides of $C_{10}$–$C_{18}$ saturated fatty acids, which allows the use of less fragrance, thus resulting in a cost savings. An especially useful member of this series is Softisan ® 100. Preferably, emollient waxes will make up about 3–10% of the composition, most preferably about 3.5–8%.

B. Polyhydric Alcohol Emollient

The emulsions of the present invention will also include one or more polyhydric alcohol emollients which are preferably $C_2$–$C_5$ alkanols substituted with 2–4 hydroxyl groups, such as propylene glycol, glycerol, and sorbitol. Polyhydric alcohol emollients will preferably make up 5–15% by weight of the emulsion. One especially preferred mixture of polyhydric alcohol emollients is an about 1:1 mixture of propylene glycol and glycerol.

Therefore, preferred emulsions useful in the present invention may be formulated so as to contain about 50–85% water, about 4–12% emollient oil, about 3.0–10% emollient wax stabilizer, about 5–20% polyhydric alcohol emollient, and about 0.5%–10% organic, water-soluble surfactant, and, optionally, about 0.025–0.75% antibacterial preservative and about 0.1 to 0.5% fragrance.

The following ingredients were combined in the weight percentages indicated in Table VI to form a moisturizing composition by the procedure described below.

TABLE VI

| INGREDIENT | PERCENT | GRAMS |
|---|---|---|
| Group A | | |
| Glyceryl Monostearate | 5.0 | 750.0 |
| Cetyl Alcohol | 0.5 | 75.0 |
| Mineral Oil | 5.0 | 750.0 |
| i-Stearyl Neopentanoate | 3.0 | 450.0 |
| Propyl Parabens | 0.10 | 15.0 |
| Butyl Parabens | 0.05 | 7.5 |
| Group B | | |
| Water (deionized) | 62.15 | 9,322.5 |
| Methyl Parabens | 0.30 | 45.0 |
| Propylene Glycol | 5.00 | 750.0 |
| Glycerol | 5.00 | 750.0 |
| Lauryl Dimethyl Amine Oxide (29–31% Solution in $H_2O$) | 3.0 | 450.0 |
| Group C | | |
| Water | 5.0 | 750.0 |
| Sodium Lauryl Sulfate | 0.50 | 75.0 |
| Fragrance | 0.30 | 45.0 |
| Water | 5.0 | 750.0 |
| Kathon CG (Preservative) | 0.10 | 15.0 |
| | 100.00 | 15,000.0 |

The oil-phase ingredients of Group A were mixed and heated to 75° C. The water-phase Group B ingredients were separately mixed, heated to 75° C. and then the Group A ingredients were added with good agitation. Stirring was contained for 10 minutes and a 23° C. solution of the Group C ingredients was added subsurface to the stirred 72° C. mixture. The emulsion was stirred and cooled to 45° C. at which point the fragrance was added. The mixture was stirred until its temperature fell to 35° C. The mixture was allowed to stand overnight and then the preservative solution was added with stirring. The mixture was stirred for 45 minutes and then used to impregnate a sheet of Crown Textile C-785 (1.25 oz/yd$^2$) via a Meyer Rod to form a one-use cosmetic applicator pad (0.25 g per 1.5 square inches of fabric).

The resultant applicator pads were moist but not sticky or unduly wet to the touch and readily applied a clear, non-sticky, homogenous film of the emollient emulsion to dry skin surfaces. The film retained these desirable characteristics when the skin was moistened prior to use of the applicator. As noted above, an effective anti-acne amount of retinoic acid can optionally be combined with this emollient composition.

V. Make-Up Remover

The present applicator system can also be used as a dual system applicator wherein one or more pads are used to apply one or more of the pigment-containing cosmetic compositions variously known as "make-up," i.e., lipstick, rouge, blush, eyeshadow, eyeliner and the like, while another of the pad or pads is impregnated with a composition that will remove the make-up, e.g., will solubilize the waxy components, or waxy base, of the make-up and cause it to be absorbed by the porous applicator pad.

A preferred make-up remover composition is disclosed in Kellett (U.S. Pat. No. 4,806,572) and comprises a wax-free mixture of about 25-75% water, about 15-70% of a water-insoluble liquid emollient oil (as described hereinabove) and an amount of surfactant (about 1-15%) effective to stabilize the aqueous phase as a homogeneous emulsion. Preferred emollient oils comprise a mixture of a mineral oil and a liquid fatty acid ester, i.e., a ($C_5$–$C_{30}$)alkyl ($C_8$–$C_{12}$)-fatty acid ester. Preferably, the surfactant is a mixture of an anionic surfactant with a nonionic polyoxyalkylene block copolymer (mw 1500-3500) in a weight ratio of about 1.5-0.75:1.

Preferred make-up remover pads comprise a resilient open-celled, hydrophilic polyurethane foam matrix, wherein said matrix integrally incorporates an aqueous phase incorporating about 25-75% water, about 15-70% of a water-insoluble liquid emollient oil, and an amount of surfactant effective to stabilize the aqueous phase so that it is released from the foam matrix as a homogenous emulsion when the pad is applied to skin, and wherein said aqueous phase contains no natural or synthetic wax.

VI. Steroids

To treat skin irritations and other dermatological conditions such as various dematoses, including chronic neurodermatitis, nummular dermatitis, atopic dermatitis, and psoriasis; eczema, poison plant rashes, insect bites and rashes due to cosmetics, detergents, jewelry and the like, one or more of the pads of the present applicators can be impregnated with an effective dermatological amount of one or more steroids, such as a corticosteroid. The pad may be impregnated with a dry powder of the steroid or steroids, optionally in combination with a solid inert carrier such as starch, talcum powder, dextrin, microcrystalline cellulose and the like. Preferably, the steroid is impregnated into the pad in combination with a pharmaceutically acceptable carrier, i.e., in combination with a suitable solvent or solvent mixture (in solution), a liquid lotion or emulsion, or an ointment or a gel.

The percentage of the steroid present in the vehicle can be varied widely, depending on the potency of the steroid with respect to the condition to be treated, but can range from about 0.025-0.05% in the case of corticosteroids such as betamethasone dipropionate or fluocinonide, up to as much as 1-5% in the case of hydrocortisone or cortisol.

Useful corticosteroids, their dermatological indications and dosages are disclosed in *Remington's Pharmaceutical Sciences*, A. Osol, ed., Mack Publishing, Easton, Pa. (16th ed. 1980) at pages 898-912, which is incorporated by reference herein, and include betamethasone, cortisol, dexamethasone, flumethasone fluocinolone, fluorometholone, flurandrenolide, methylprednisolone, prenisolone, desoximetasone, diflorasone, triamcinolone, and their nontoxic organic acid salts such as the benzoate, acetate, valerate, pivalate, acetonide, acetonide-acetate, diacetate, butyrate, dipropionate and valerate salts, and the like.

In combination with the appropriate carrier, if any, the steroid will be impregnated into the applicator pad so that, upon application of the pad to the afflicted skin area, an effective amount of steroid will be delivered to the skin, e.g., from about 500 μg-250 mg of total steroid per m$^2$ of skin, depending upon the steroid or steroids present in the composition.

Two representative steroid-containing solutions comprising mixtures of organic solvents as the carrier vehicle are given in Table VII below.

TABLE VII

| Steroid Solutions | | |
|---|---|---|
| | Formulation (wt-%) | |
| Ingredient | A | B |
| Propylene glycol | 86.18 | 82.95 |
| Isopropyl alcohol | 12.00 | 7.00 |
| m-Pyrrol | 1.75 | — |
| Carbitol | — | 10.00 |
| Betamethasone dipropionate | 0.64 | — |
| Fluocinonide (Lidex ™) | — | 0.05 |

The steroid can also be microencapsulated or stabilized by absorption onto or into dextrin or cyclodextrin particles by methods known to the art.

As noted above, when a steroid-containing composition is included in one of the pads, the other pad or pads can contain dermatological agents which complement or enhance the activity of the steroid. Such ingredients include antihistamines, antibiotics, e.g., in combination with the carrier vehicles described above, emollient compositions such as those disclosed above, anti-fungal agents, sunscreens as disclosed above, and compositions which will enhance penetration of the steroid into the skin. The latter compositions include those which, following their application, form an occlusive barrier or film over the applied film of steroid-containing composition. Such barrier-forming compositions include those which comprise solvent-dissolved or dispersed film-forming polymers such as polysaccharides, polyvinylalcohols, polyacrylate salts, and/or cross-linked polyacrylate hydrogels.

Any of the above-described compositions can be preformulated and applied to the pads, which have been preattached to the base or cover sheet, by dipping, spraying or brushing techniques well known to the art.

In practice, the user, e.g., a human afflicted with acne, would either expose the medicated pads and apply them sequentially or simultaneously to the afflicted area. For example, the user might first expose a pad impregnated with Retin ® A or an anti-acne antibiotic, i.e., erythromycin or clindamycin or a pharmaceutically acceptable salt thereof, either dissolved in a non-toxic organic solvent, or dispersed in a gelled vehicle, such as that described in conjunction with Table IV, above. After applying the antibiotic pad to the afflicted skin area, the user would expose the second pad impregnated with peroxide in one of the vehicles described in conjunction with Tables I-III, above, or a pad impregnated with salicylic acid-containing vehicle. This same skin area would then be contacted with the second pad, in order to combine the two active ingredients in situ. Alternatively, the user could expose two adjacent pads, and apply the adjacent pads essentially simultaneously to the skin, to deposit, for example, a mixture of antibiotic- and peroxide-containing vehicles thereto, preferably in a homogeneous, even film.

Each composition will be absorbed into a single pad in an amount effective to provide a unit dosage of each of the bioactive ingredients therein. It is to be understood that such a dose can vary widely, as it will be based on the size of skin area to be treated, and the nature and severity of the dermatological condition to be treated. For example, the amount of a given liquid, semi-liquid or gelled composition delivered to the skin of the user may vary from as little as 0.25-0.5 g to as much as 1-3 g, depending upon the choice of active ingredient, the size of pad and type of material of which it is constructed and the skin area and condition to be treated. Thus, the amount of active ingredient delivered as a unit dose can be preselected, using the weight percentages provided hereinabove as guidelines.

All patents, patent applications and other documents cited hereinabove are incorporated by reference herein. The invention has been described with reference to various specific and preferred embodiments and techniques. However, it should be understood that many variations and modifications may be made while remaining within the spirit and scope of the invention, and the invention is not to be construed as limited to the specific embodiments shown in the drawings.

What is claimed is:

1. A method for applying a plurality of dermatological agents to the skin from one dispensing and applicator system comprising the steps of:
   (a) providing a dispensing and applicator system comprising:
   (1) a first and second flexible, moisture impermeable cover sheet;
   (2) a first applicator pad and a second applicator pad affixed to a first surface of said first and second cover sheets, respectively; said first pad being impregnated with a first composition comprising a first dermatological agent and said second pad being impregnated with a second composition comprising a second dermatological agent; and
   (3) a flexible, moisture impermeable support sheet having the peripheral surface of its first side releasably sealed by means of a first continuous seal line to the opposed peripheral surface of the first cover sheet so as to form a first compartment containing the first pad attached t said surface of first cover sheet; and having the peripheral surface of its second side releasably sealed by means of a second continuous seal line to the opposed peripheral surface of the second cover sheet so as to form a second compartment containing said second pad attached to said second cover sheet, which seal lines are positioned inwardly from the edges of the sheets over a portion of the opposed peripheral surfaces, so as to form two pairs of opposed flanges;
   (b) sequentially manually grasping and separating each pair of opposed flanges to at least partially release each cover sheet from the support sheet, so that said first pad and said second pad are exposed; and
   (c) contacting said first pad and said second pad with the skin to release the compositions sequentially from the pads, to thereby apply a film of the agents onto the skin.

2. A method for applying a plurality of dermatological agents to the skin from one dispensing and applicator system comprising the steps of:
   (a) providing a dispensing and applicator system comprising:
   (1) a first and second flexible, moisture impermeable cover sheet;
   (2) a first and second applicator pad each affixed to a first surface of said first and second cover sheets, respectively, said first pad being impregnated with a first composition comprising a first dermatological agent and said second pad being impregnated with a second composition comprising a second dermatological agent; and
   (3) a flexible, moisture impermeable support sheet having the peripheral surface of its first side releasably sealed to the opposed peripheral first surface of the first cover sheet by a first continuous seal line, so as to form a first compartment containing the first pad attached to said first surface of the first cover sheet; and said second cover sheet having the peripheral surface of its first surface releasably sealed to the opposed second peripheral surface of the second surface of the first cover sheet by a second continuous seal line, so as to form a second compartment containing said second pad attached to the first surface of said second cover sheet, which seal lines are positioned inwardly from the edges of the sheets over a portion of the opposed peripheral surfaces, so as to form two pairs of opposed flanges;
   (b) sequentially manually grasping and separating each of the pairs of flanges to release the second cover sheet from the first cover sheet and then to release the first cover sheet from the support sheet, so that said pads are exposed; and
   (c) contacting the pads with the skin to release the compositions sequentially from the pads, to thereby apply a film of the compositions onto the skin.

3. A method for applying a plurality of dermatological agents to the skin from one dispensing and applicator system comprising the steps of:
   (a) providing a dispensing and applicator system comprising:

(1) a flexible, moisture impermeable support sheet having a first side and a second side;

(2) a first applicator pad affixed to the first side of said support sheet, and a second applicator pad attached to the second side of said support sheet, said first pad being impregnated with a first composition comprising a first dermatological agent and said second pad being impregnated with a second composition comprising a second dermatological agent; and (3) a first flexible, moisture impermeable cover sheet having a first peripheral surface of a first side releasably sealed by a continuous seal line to the peripheral surface of the first side of said support sheet; and a second flexible moisture impermeable cover sheet, having a first peripheral surface of a first side releasably sealed by a continuous seal line to the peripheral surface of the second side of said support sheet; so as to form two compartments each containing one of said pads, each compartment being defined by a continuous seal line, which seal lines are positioned inwardly from the edges of the sheets over a portion of the opposed peripheral surfaces, so as to form two pairs of opposed flanges;

(b) sequentially manually grasping and separating each pair of the flanges to release each cover sheet from the support sheet, so that said pads are exposed; and (c) contacting the pads with the skin to release the compositions sequentially from the pads, to thereby apply a film of the compositions onto the skin.

4. The method of claims 1, 2 or 3 wherein the cover sheet and support sheet are made of a deformable plastic coated foil.

5. The method of claims 1, 2 or 3 wherein the cover sheet and the support sheet are sealed together by heat sealing or by an adhesive.

6. The method of claims 1, 2 or 3 wherein the applicator pads are made of natural fiber, synthetic fiber or foam.

7. The method of claims 1, 2 or 3 wherein the first dermatological agent is an effective anti-acne amount of a peroxide.

8. The method of claim 7 wherein the first dermatological agent comprises benzoyl peroxide.

9. The method of claim 7 wherein the first applicator pad is impregnated with a first composition comprising an effective anti-acne amount of an organic peroxide in combination with an aqeuous gel comprising about 40-75% water, about 0.25-5% of an inorganic gelling agent, and about 2.5-10% of a mixture of an inorganic emollient oil and an emollient organic ester.

10. The method of claim 9 wherein the first composition further comprises about 0.025-0.25% of an amphoteric surfactant.

11. The method of claim 10 wherein the first composition further comprises about 10-20% of a $(C_2-C_4)$alkanol.

12. The method of claim 7 wherein the first applicator pad is impregnated with a first gelled composition comprising an effective anti-acne amount of an organic peroxide dispersed in about 50-80% water in combination with an effective amount of an inorganic gelling agent.

13. The method of claim 7 wherein the first applicator pad is impregnated with a first gelled anhydrous composition comprising an effective anti-acne amount of an organic peroxide, about 75-90% of a mixture of inorganic and organic emollient oils, and about 1-10% of an inorganic gelling agent.

14. The method of claim 13 wherein the composition further comprises about 0.1-1% of an amphoteric surfactant.

15. The method of claim 7 wherein the second dermatological agent is an effective anti-acne amount of an antibiotic selected from the group consisting of erythromycin, tetracycline, clindamycin and the pharmaceutically acceptable salts thereof.

16. The method of claim 15 wherein the antibiotic is clindamycin or a pharmaceutically acceptable salt thereof.

17. The method of claim 15 wherein the second composition comprises about 0.1-5% of the antibiotic dissolved or dispersed in mixture of water and a water-miscible organic solvent.

18. The method of claim 17 wherein the second composition comprises an emulsion of about 0.1-5% clindamycin, erythromycin or a pharmaceutically acceptable salt thereof, about 80-95% aqueous alcohol and about 5-15% emollient organic esters.

19. The method of claims 1, 2 or 3 wherein the first dermatological agent is an effective keratolytic amount of salicylic acid.

20. The method of claim 19 wherein the first composition comprises an aqueous-alcohol gel comprising about 0.5-10% salicylic acid.

21. The method of claim 20 wherein the gel comprises about 0.5-5% of an organic gelling agent.

22. The method of claims 1, 2, or 3 wherein the first dermatological agent is an effective anti-acne amount of retinoic acid.

23. The method of claim 22 wherein the first dermatological composition comprises about 0.01-0.25% retinoic acid.

24. The method of claim 23 wherein the first dermatological composition further comprises a gelled mixture of water with a water-miscible organic solvent.

25. The method of claim 22 wherein the first dermatological composition comprises about 0.01-25% retinoic acid, about 50-85% water, about 4-12% emollient oil, about 3-10% emollient wax stabilizer, about 5-20% polyhydric alcohol emollient and about 0.5-10% organic, water-soluble surfactant.

26. The method of claim 22 wherein the second dermatological composition comprises an effective amount of one or more sunscreen compounds.

27. The method of claim 22 wherein the second dermatological composition comprises about 50-85% water, about 4-12% emollient oil, about 3-10% emollient wax stabilizer, about 5-20% polyhydric alcohol emollient and about 0.5-10% organic, water-soluble surfactant.

28. The method of claims 1, 2 or 3 wherein the first dermatological composition comprises an effective amount of one or more sunscreen compounds.

29. The method of claim 27 wherein the second dermatological composition comprises an effective amount of one or more sunscreen compounds.

30. The method of claims 1, 2 or 3 wherein the first composition is a pigment-containing wax-based cosmetic composition and the second composition is a make-up remover composition comprising a wax-free mixture of about 25-75% water, about 15-70% of a water-insoluble liquid emollient oil and an amount of a surfactant effective to stabilize the mixture as a homogeneous emulsion.

31. The method of claim 30 wherein the first applicator pad is a hydrophilic polyurethane foam pad.

32. The method of claim 7 wherein the first dermatological agent is an effective dermatological amount of corticosteroid.

33. The method of claim 32 wherein the corticosteroid is dispersed throughout the first applicator pad as a powder.

34. The method of claim 32 wherein the first applicator pad is impregnated with a corticosteroid in combination with a pharmaceutically acceptable carrier.

35. The method of claim 32 wherein the second dermatological agent is an antihistamine, an antibiotic, an antifungal agent, a sunscreen, an emollient or a film-forming polymer.

* * * * *